US006352848B1

(12) United States Patent
Altenbuchner et al.

(10) Patent No.: US 6,352,848 B1
(45) Date of Patent: *Mar. 5, 2002

(54) **RECOMBINANT L-N-CARBAMOYLASE FROM *ARTHROBACTER AURESCENS* AND METHOD OF PRODUCING L-AMINO ACIDS THEREWITH**

(75) Inventors: Josef Altenbuchner, Nufringen; Ralf Mattes, Stuttgart; Markus Pietzsch, Stuttgart; Christoph Syldatk, Stuttgart; Anja Wiese, Stuttgart; Burkard Wilms, Stuttgart, all of (DE)

(73) Assignees: Degussa-Huls Aktiengesellschaft, Marl; Universitat Stuttgart, Allmandring; Roche Diagnostics GmbH, Mainheim, all of (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,055

(22) Filed: Apr. 2, 1999

(30) Foreign Application Priority Data

Apr. 2, 1998 (DE) .......................................... 198 14 813

(51) Int. Cl.[7] .............................. C12N 9/14; C12N 9/48; C12N 9/78; C12N 9/80; C12N 1/20
(52) U.S. Cl. ........................ 435/195; 435/183; 435/212; 435/227; 435/228; 435/252.3; 435/320.1; 536/23.2
(58) Field of Search ................................. 435/106, 183, 435/195, 252.3, 320.1, 212, 227, 228; 536/23.2

(56) References Cited

U.S. PATENT DOCUMENTS 5,516,660 A * 5/1996 Wagner et al. .............. 435/109
5,827,717 A * 10/1998 Wagner et al. .............. 435/195

FOREIGN PATENT DOCUMENTS

EP 0 625 571 11/1994
FR 2 728 905 7/1996

OTHER PUBLICATIONS

GenBank Accession No. 085664, dated Nov. 1, 1998.*
Siemann et al. Characterization of serological properties of polyclonal antibodies produced against enaymes involved in the L–selective cleavage of hydantoin derivatives. Biotechnol. Lett., Jan. 1993, vol. 15(1):1–6.*
Wilms et al., "Cloning, nucleotide sequence and expression of a new L–N–carbamoylase gene from *Arthrobacter aurescens* DSM 3747 in *E. coli*", Journal of Biotechnology, vol. 68, 1999, p. 101–113.
Siemann et al., "Detection and Comparison of strains with selective l–hydantoin cleaving activity using polyclonal antibodies", Biotechnology Tecniques, vol. 7, No. 5, 1993, p. 361–366.
Gross et al., "Screening method for microorganisms producing L–aminoacids from D, L–5–monosubstituted hydantoins", Biotechnology Techniques, vol. 1, No. 2, 1987, p. 85–90.
English language abstract of JR above.
English language abstract of KR above.

* cited by examiner

*Primary Examiner*—Rebecca E. Prouty
*Assistant Examiner*—Manjunath N. Rao
(74) *Attorney, Agent, or Firm*—Pillsbury Winthrop LLP

(57) ABSTRACT

A novel rec-L-N-carbamoylase from *Arthrobacter aurescens* and its method of use for producing L-amino acids. The recombinantly produced L-carbamoylase is unexpectedly stable, so that an industrial method of producing L-amino acids can be established with it, in contrast to previously known L-carbamoylases.

5 Claims, 2 Drawing Sheets

SEQUENCE LISTING

```
<160> NUMBER OF SEQ ID NOS: 2

<210> SEQ ID NO 1
<211> LENGTH: 1239
<212> TYPE: DNA
<213> ORGANISM: Arthrobacter aurescens

<400> SEQUENCE: 1
gtgaccctgc agaaagcgca agcggcgcgc attgagaaag agatccggga gctctcccgg      60
ttctcggcag aaggccccgg tgttacccgg ctgacctaca ctccagagca tgccgccgcg     120
cgggaaacgc tcattgcggc tatgaaagcg gccgccttga gcgttcgtga agacgcactc     180
ggaaacatca tcggccgacg tgaaggcact gatccggagc ttcctgcgat cgcggtcggt     240
tcacacttcg attctgtccg aaacggcggg atgtttgatg gcactgcagg cgtggtgtgc     300
gcccttgagg ctgcccgggt gatgctggag aacggctacg tgaatcggca tccatttgag     360
ttcatcgcga tcgtggagga ggaaggggcc cgcttcagca gtggcatgtt gggcggccgg     420
gccattgcag ggttggtcgc cgacaggaa ctggactctt tggttgatga ggatggagtg      480
tccgttaggc aggcggctac tgccttcggc ttgaagccgg cgaactgca ggctgcagcc      540 cgctccgcgg cggacctgcg tgcttttatc gaactacaca ttgaacaagg accgatcctc     600
gagcaggagc aaatagagat cggagttgta acctccatcg ttggcgttcg cgcattgcgg     660
gttgccgtca aaggcagaag cgaccacgcc ggcacaaccc ccatgcacct gcgccaggat     720
gcgctggtac ccgccgctct catggtgagg gaggtcaacc ggttcgtcaa cgagatcgcc     780
gatggcacag tggctaccgt tggccacctc acagtggccc ccggtggagg caaccaggtc     840
ccgggggagg tggacttcac actggacctg cgttctccgc atgaggagtc gctccgcgtg     900
ctgatcgacc gcatctcggt catggtcggc gaggtcgcct cccaggccgg tgtggctgcc     960
gatgtggatg aattttttcaa tctcagcccg gtgcagctgg ctcctaccat ggtggacgcc    1020
gttcgcgaag cggcctcggc cttgcagttc acacaccggg atatcagcag tggggcgggc    1080
cacgactcga tgttcatcgc ccaggtcacg gacgtcggaa tggttttcgt tccaagccgt    1140
gctggccgga gccacgttcc cgaagaatgg accgatttcg atgaccttcg caaaggaact    1200
gaggttgtcc tccgggtaat gaaggcactt gaccggtaa                          1239
```

```
<210> SEQ ID NO 2
<211> LENGTH: 412
<212> TYPE: PRT
<213> ORGANISM: Arthrobacter aurescens

<400> SEQUENCE: 2

Met Thr Leu Gln Lys Ala Gln Ala Arg Ile Glu Lys Glu Ile Arg
 1               5                  10                  15

Glu Leu Ser Arg Phe Ser Ala Glu Gly Pro Gly Val Thr Arg Leu Thr
                20                  25                  30

Tyr Thr Pro Glu His Ala Ala Arg Glu Thr Leu Ile Ala Ala Met
                35                  40                  45

Lys Ala Ala Leu Ser Val Arg Glu Asp Ala Leu Gly Asn Ile Ile
    50                  55                  60

Gly Arg Arg Glu Gly Thr Asp Pro Glu Leu Pro Ala Ile Ala Val Gly
 65                  70                  75                  80

Ser His Phe Asp Ser Val Arg Asn Gly Gly Met Phe Asp Gly Thr Ala
                    85                  90                  95

Gly Val Val Cys Ala Leu Glu Ala Ala Arg Val Met Leu Glu Asn Gly
                   100                 105                 110

Tyr Val Asn Arg His Pro Phe Glu Phe Ile Ala Ile Val Glu Glu Glu
                   115                 120                 125

Gly Ala Arg Phe Ser Ser Gly Met Leu Gly Gly Arg Ala Ile Ala Gly
                   130                 135                 140

Leu Val Ala Asp Arg Glu Leu Asp Ser Leu Val Asp Glu Asp Gly Val
145                 150                 155                 160

Ser Val Arg Gln Ala Ala Thr Ala Phe Gly Leu Lys Pro Gly Glu Leu
                   165                 170                 175

Gln Ala Ala Arg Ser Ala Ala Asp Leu Arg Ala Phe Ile Glu Leu
                   180                 185                 190

His Ile Glu Gln Gly Pro Ile Leu Glu Gln Glu Gln Ile Glu Ile Gly
                   195                 200                 205

Val Val Thr Ser Ile Val Gly Val Arg Ala Leu Arg Val Ala Val Lys
                   210                 215                 220

Gly Arg Ser Asp His Ala Gly Thr Thr Pro Met His Leu Arg Gln Asp
225                 230                 235                 240

Ala Leu Val Pro Ala Ala Leu Met Val Arg Glu Val Asn Arg Phe Val
                   245                 250                 255

Asn Glu Ile Ala Asp Gly Thr Val Ala Thr Val Gly His Leu Thr Val
                   260                 265                 270

Ala Pro Gly Gly Gly Asn Gln Val Pro Gly Glu Val Asp Phe Thr Leu
                   275                 280                 285

Asp Leu Arg Ser Pro His Glu Glu Ser Leu Arg Val Leu Ile Asp Arg
                   290                 295                 300

Ile Ser Val Met Val Gly Glu Val Ala Ser Gln Ala Gly Val Ala Ala
305                 310                 315                 320

Asp Val Asp Glu Phe Phe Asn Leu Ser Pro Val Gln Leu Ala Pro Thr
                   325                 330                 335

Met Val Asp Ala Val Arg Glu Ala Ala Ser Ala Leu Gln Phe Thr His
                   340                 345                 350

Arg Asp Ile Ser Ser Gly Ala Gly His Asp Ser Met Phe Ile Ala Gln
                   355                 360                 365

Val Thr Asp Val Gly Met Val Phe Val Pro Ser Arg Ala Gly Arg Ser
                   370                 375                 380
```

-continued

```
His Val Pro Glu Glu Trp Thr Asp Phe Asp Asp Leu Arg Lys Gly Thr
385                 390                 395                 400

Glu Val Val Leu Arg Val Met Lys Ala Leu Asp Arg
                405                 410
```

RECOMBINANT L-N-CARBAMOYLASE FROM *ARTHROBACTER AURESCENS* AND METHOD OF PRODUCING L-AMINO ACIDS THEREWITH

CROSS-REFERENCE TO RELATED APPLICATION

This application claims priority from German Application No. 198 14 813.5, filed on Apr. 2, 1998, the entire disclosure of which is hereby incorporated herein by reference.

BACKGROUND OF THE INVENTION

1. Field of the Invention

The present invention relates to a novel recombinant (rec-) L-N-carbamoylase from *Arthrobacter aurescens* as well as to a method of producing L-arnino acids with this carbamoylase.

The L-amino acids which can be advantageously produced with the novel rec-carbamoylase are important chiral starting materials for the organic synthesis, for example, of drugs and have significance in human and animal nourishment.

2. Background Information

The advantageous possibility of the stereoselective splitting of the D,L-carbamoyl amino acids assessable from the corresponding hydantoins by hydantoinases by means of L-N- and/or D-N-carbamoylases resulted previously in the establishment of methods for the production of L- and D-amino acids on an industrial scale. L-specific carbamoylases have been detected in very different strains of microorganisms (Ogawa et al., J. Mol. Cal. B: Enzym. 1997, 2, 163–176; Syldatk et al. in Drauz, K. and Waldmann, H.: Enzyme Catalysis in Organic Synthesis, Weinheim: VCH-Verlag, 1995).

The presence of L-N-carbamoylase activity in cells of the strain *Arthrobacter aurescens* has been known for some time. This carbamoylase has been isolated in homogeneous form and the N-terminal sequence has been determined. (Müller, dissertation, Braunschweig TU Technical University, 1990). However, the gene coding for the enzyme was unknown and has therefore not been previously cloned or overexpressed. Thus, the recombinant enzyme and its amino acid sequence and the DNA coding the amino acid sequence were previously unknown.

Three L-carbamoylases produced in a recombinant manner have been described in the literature (Batisse et al., Appl. Environ. Microbiol. 1997, 63, 763–766; Mukohara et al., Biosci. Biotechn. Biochem. 1993, 57, 1935–1937; Watabe et al., J. Bacteriology 1992, 174, 962–969). However, the L-carbamoylases cited there are relatively unstable and are thus unsuitable for being used in an industrial process.

The L-specific carbamoylase from *Arthrobacter aurescens* (A.a.) was able to be used previously for the splitting of N-carbamoyl amino acids to free L-amino acids only as a predominantly homogeneously purified enzyme or in the form of free or immobilized, dormant [resting] whole cells. Several basic problems occur in the latter method. They include, among other things, transport limitations (especially for the N-carbamoyl amino acids), potential side reactions (degradation of the formed amino acids by other enzymes present) as well as contaminants in the product caused by lysis of the whole cells used, which make expensive purification processes necessary.

The L-carbamoylase from A.a. is very unstable in both forms used, which can be traced in the instance where dormant, immobilized cells are used to the natural protein turnover of the enzyme (Siemann, dissertation, Braunschweig TU, 1992). When used as a homogeneously purified enzyme, the lability is obviously affected by unavoidable changes in the protein concentration and the salt content. Moreover, the sensitivity of the wild enzyme to oxidation has been observed. In addition, only a very low yield of 2.7% is achieved in the purification of carbamoylase from the wild strain (Müller dissertation, Braunschweig TU, 1990). This low yield, the necessary complicated purification method, and the previously immanent lability of the enzyme prevent the use of this procedure in a competitive industrial method for obtaining L-amino acids.

The present invention therefore had the objective of obtaining an L-carbamoylase which is more stable than the L-carbamoylases of the prior art, and those previously producible from *Arthrobacter aurescens*, in a simpler form and with a better yield. However, the further requirements which a method places on the enzyme used on an industrial scale such as, for example, activity or selectivity regarding substrate and stereochemistry, etc. should not be negatively affected.

These and other problems not cited in detail but which will be evident to those of skill in the art are solved by rec-L-N-carbamoylase from *Arthrobacter aurescens* and mutants thereof, which are included in the invention. Their amino acid sequences and gene sequences derived therefrom are also included in the invention, as well as vectors modified with the gene sequences, corresponding plasmids, modified host organisms and cells of the host organisms.

In addition, the invention includes an advantageous method of producing L-amino acids using these enzymes of the invention.

As a result of the fact that L-N-carbamoylase is produced in a recombinant manner from *Arthrobacter aurescens* or its mutants, L-carbamoylases are obtained in very good yields of >90% and with a decidedly high purity which have a much greater stability over the previously known carbamoylases, yet have a good activity and very good stereoselectivity as concerns the regarded biotransformation. These characteristics are essential for the successful use of carbamoylases in an industrial method for the production of L-amino acids.

It resulted in stability studies that homogeneously purified carbamoylase has only a few minutes activity at 50° C. (Müller dissertation, Braunschweig TU, 1990), whereas on the other hand rec-carbamoylase is active for hours. At 37° C. the activity of rec-carbamoylase is almost unchanged for 100 h (FIG. 2). This could in no way have been foreseen and is nevertheless all the more advantageous.

In addition thereto, the use of these recombinant carbamoylases opens up the possibility for the first time of obtaining industrial access to β-aryl-substituted L-amino acids by means of an enzymatic biotransformation via (D,L)-N-carbamoyl amino acids. The regarded carbamoylase is the only one of the previously known carbamoylases to also offer, in addition to the high L-enantioselectivity, the possibility of reacting [converting] β-aryl-substituted L-N-carbamoyl amino acids to an extent sufficient for an industrial method. (D,L)-formyl amino acids of this provenance are also suitable for being reacted with the enzymes in accordance with the invention. The free L-amino acid is also obtained with preference from the latter [formyl amino acids].

The amino acid sequences characterizing the recombinant L-N-carbamoylase from *Arthrobacter aurescens* and its mutants only have an agreement of maximally 38% with amino acid sequences of L-N-carbamoylases known from the state of the art. The novel and inventive gene sequences coding these amino acid sequences can be produced according to known biochemical methods. The vectors, plasmids and cells of host organisms containing these gene sequences are also novel and inventive. Preferred plasmids are pAW 16 and pAW 178-2 (FIG. 1), a preferred vector is pJOE 2702. Host cells can be in principle all microorganisms known to the expert in the art and coming into consideration for this purpose; however, *E. coli* JM 109 or *E. coli* W3 110 is preferred.

The induction of the expression can be achieved in principle with all methods known to the expert in the art. However, rhamnose-, IPTG-and lactose systems are preferred.

The isolation and expression of the L-N-carbamoylase gene hyuC from *Arthrobacter aurescens* takes place as follows.

A gene bank representative for the entire genome of *Arthrobacter aurescens* and in an *E. coli* λTRESIII vector was prepared and screened with an oligonucleotide which was derived from the N-terminal amino acid sequence of the purified hydantoinase from *Arthrobacter aurescens*. Plasmid pAW16 was obtained thereby which contained a 7.6 kb DNA fragment of *Arthrobacter aurescens*. Its nucleotide sequence was completely determined. The hydantoinase gene was identified from the nucleotide sequence. Another reading frame was identified on the C-terminal end of the hydantoinase gene, the derived amino acid sequence of which reading frame exhibited homology to an N-L-carbamoylase from *Pseudomonas sp.* and *Bacillus stearothermophilus*. Moreover, the start of the derived protein exhibited agreement with the N-terminal end, which was determined by amino acid sequencing, of the L-N-carbamoylase purified from *Arthrobacter aurescens*. The carbamoylase gene was amplified using PCR from pAW16 and inserted into an *E. coli* expression vector. Carbamoylase can be produced in the recombinant cells in a high amount via a promoter which can be induced by the sugar rhamnose.

SEQ ID NO: 1 and SEQ ID NO:2 set forth the nucleotide and amino acid sequences, respectively, of the rec-carbamoylase from A.a.

The term "mutants of L-carbamoylase" will be understood by the skilled artisan to mean enzymes which are produced by the exchange of individual amino acids, if necessary, but are derived from the rec-carbamoylase from A.a., and which conform to the characteristics outlined above, for use in the described method in a manner. Such mutants will be at least as good and possibly better (for workup, lesser sensitivity to oxidation, etc.). The term "mutants" also denotes such enzymes which are produced by the addition of amino acids or amino acid sequences to the rec-enzyme. Those are preferred which exhibit an His-TAG or Asp-TAG modification on the C-terminus.

The desired L-amino acids are produced in accordance with the invention with these advantageous L-N-carbamoylases from the corresponding L-N-carbamoyl amino acids and L-N-formyl amino acids. As has already been stated, the claimed L-N-carbamoylases exhibit a preferred reaction of β-aryl-substituted L-N-carbamoyl- and L-N-formyl amino acids. These chiral compounds can be produced from chiral hydantoins preferably by hydantoinases. The additional use of a chemical or enzymatic method for the racemization of hydantoins makes it possible in an extremely advantageous manner to construct an industrially valuable process for the obtention of L-amino acids from readily producible hydantoins. Chiral 5-monosubstituted hydantoins with aromatic side chains are to be considered with preference thereby. The stereoisomers of these hydantoins are constantly equilibrated by the established racemization step—if necessary, by a racemase—whereas the hydantoinase brings forth the corresponding L- or D,L-N-carbamoyl amino acids. The stereospecific rec-L-N-carbamoylases of the invention then assure the last step for the production of the L-amino acid since the hydantoinase from A.a. exhibits no absolute stereospecificity, in contrast to the carbamoylase. The preceding constant equilibration of the stereoisomers of the hydantoins assures that all hydantoin, whether D- or L-configured, is finally converted to an L-amino acid.

The protected amino acids are preferably reacted with the enzymes in a so-called enzyme membrane reactor. The stability of the enzymes used assures that the enzymes retained by an ultrafiltration membrane in the reactor can be used several times (>10 times) in succession for the production of L-amino acid. This saves expense and complexity for the method since only substrate must be charged and product drawn off.

Alternatively, the enzyme can be immobilized on carriers. This was successful in sufficiently high yield after the rec-enzyme was able to be used in pure form. All methods (covalent, adsorptive, etc.) known to the expert in the art for the immobilization of enzymes on carrier materials (silica gels, $SiO_2$, EAH sepharose, nitrocellulose, Eupergit®) can be used; however, the covalent coupling to EAH sepharose obtained by carbodiimide is advantageous. When modified in this manner the enzyme can also be used in a fixed-bed reactor.

The following examples are intended to explain the invention without, however, limiting it in any manner.

BRIEF DESCRIPTION OF THE DRAWINGS

FIG. 1 shows the plasmid pAW178.2 which may be used in connection with the cloning of the L-N-carbamoylase DNA.

FIG. 2 depicts the results of an assay measuring the activity of recombinant L-N-carbamoylase.

DETAILED DESCRIPTION OF THE INVENTION

EXAMPLES

Figure 1:
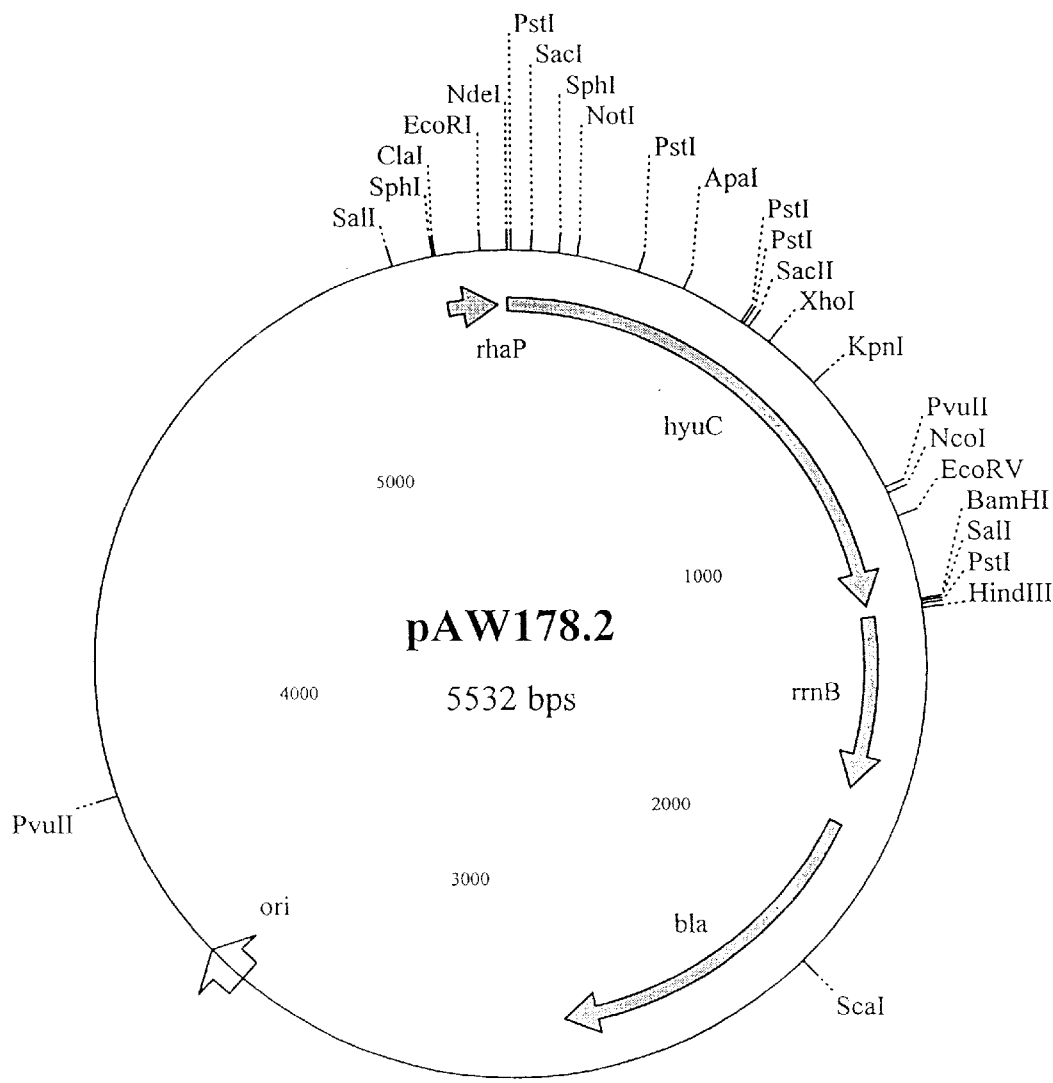
FIG. 1.

Isolation of the total DNA from *Arthrobacter aurescens:*

180 ml of the yeast extract medium K2 (bacto-peptone 4.0 g, yeast extract, 4.0 g glycine, 7.5 g, $KH_2PO_4$ 2.0 g, $K_2HPO_4$ $H_2O$ 4.0 g, pH 7.0 in 1000 ml $H_2O$) were seeded with *Arthrobacter aurescens* and incubated at 30° C. under agitation (200 rpm). The cells were harvested by centrifugation in a Sorvall GSA rotor at 4° C., 6000 rpm, 10 min, the pellet washed in 20 ml TE buffer (10 mM TRIS-HCl, 1 mM EDTA, pH 8.0), re-centrifuged as before and re-suspended in 16 ml TES buffer (25 mM TRIS-HCl, 25 mM EDTA, 10% sucrose, pH 8.0). 2 ml lysozyme solution (100 mg/ml TES buffer) was added and incubated 60 min at 37° C. for cell lysis. Then, 2 ml 10% Na-lauryl-sarcosinate and 2 ml proteinase K (10 mg/ml) were added and the mixture incubated another 60 min at 37° C. Then, 20 g CsCl and 0.6 ml ethidium bromide (10 mg/ml) were added and the mixture centrifuged at 35000 rpm, 17° C., T1270 rotor 48 hours in a Sorvall ultracentrifuge. The DNA was identified using UV light, drawn off via a single-use syringe from the centrifuge tube and dialyzed for 2 h against 2 liters TE buffer. The ethidium bromide was removed by a double phenol extraction with 2 ml neutralized phenol each time and the DNA solution again dialyzed twice against 2 l TE buffer each time.

Construction of the λ Gene Bank:

10 μg genomic DNA from *Arthrobacter aurescens* was treated with 0.75 units of the restriction enzyme XhoII for 30 min at 37° C. The genomic DNA was only partially cut thereby. The DNA was separated in a 0.7% "low melting agarose gel", the DNA rendered visible by UV light and an agarose block with fragments with a size between 7 kb to 13 kb cut out. The agarose block was melted at 65° C. in a volume of 500 μl buffer (TE buffer with 0.5 M NaCl), extracted with the same amount of phenol, and agarose and phenol separated off by centrifugation at 4° C. in an Eppendorf centrifuge at 13000 rpm, 30 min, 4° C. The aqueous phase was compounded with one tenth the volume 3 M Na acetate, pH 6.2 and 2.5 volumes ethanol, incubated 30 min at −70° C., centrifuged 10 min in an Eppendorf centrifuge, the liquid removed and the precipitated DNA washed with 100 μl 70% ethanol, air-dried and re-suspended in 10 μl TE buffer. The λRESIII vector DNA was prepared as described in Sambrook et al. (Molecular Cloning: A Laboratory Manual, Cold Spring Harbor Laboratory Press, 1989). The phage is a substitution vector, that is, a restriction fragment is removed from the vector DNA and replaced by another fragment. The phage is incapable of multiplying without insert (Altenbuchner, 1993). In this instance a 9 kb BamII fragment with the bacterial lux genes was removed from the vector in that 1 μg vector DNA was treated with 10 units BamII 1 h, the DNA separated using "low melting agarose" and the DNA of the λ arms was purified using the gel as described above. The DNA's were subsequently ligated in that approximately 25 ng of both vector arms were each incubated with 25 ng XhoII of cut fragments of *A. aurescens* in a volume of 10 μl, ligase buffer of the producer (Boehringer GmbH) and 0.5 unit ligase overnight at 17° C. 2 μl of the batch was placed into an in vitro packaging system and packed in phage particles. The packaging batch was produced as described in Sambrook et al. from the two *E. coli* strains *E. coli* BHB2690 (sonified extract, SE) and BHB2688 (freeze-thaw extract FE). For packaging 7 μl buffer A (20 mM TRIS-HCl, 3 mM $MgCl_2$, 0.05% (V/V) 2-mercaptoethanol, 1 mM EDTA, pH 8.0), 10 μl FE extract, 6 μl SE extract, 1 μl buffer M1 (113 μl $H_2O$, 3 μl 1 M TRIS-HCI, pH 7.5, 300 μg 0.05 M spermine, 0.1 M putrescine, 75 μl 0.1 M ATP, 1 μl 2 mercaptoethanol, 9 μl 1 M $MgCl_2$) and 2 μl DNA from the ligation batch were mixed and incubated 1 h at 25° C. The packaging was stopped by the addition of 0.5 ml SM buffer (5.8 g NaCl, 2 g $MgSO_4$ $H_2O$, 50 ml 1 M TRIS-HCl, pH 7.5, 2 g gelatin, per 1 l) and one drop toluene.

Identification of a Recombinant Phage with Hydantoinase Gene by Plaque Hybridization:

The phage lysate obtained from the in vitro packaging was diluted in SM buffer to approximately 5000 phages/ml. 0.1 ml dilute phage lysate was incubated with 0.1 ml overnight culture in $LB_{mal}$ of the *E. coli* strain TAP90 for 5 min at room temperature, taken up in 3 ml $LB_{mal}$ soft agar, poured on an LB plate and incubated overnight at 37° C. ($LB_{mal}$: 10 g bacto-tryptone, 5 g yeast extract, 10 g NaCl, 2 g maltose, per 1 liter $H_2O$, pH 7.5; LB agar plates: like $LB_{mal}$ without maltose with 1.5% agar, $LB_{mal}$ soft agar like $LB_{mal}$ with 0.7% agar). During this time visible plaques developed on the plate. A nylon filter (Quiabrane, Quiagen GmbH) was placed on the agar plate and the phage DNA in the plaques transferred onto the filter as a result thereof. The DNA on the filter was denatured for 5 min by placing the filter onto a stack of Whatmann paper which had been impregnated with denaturation solution (0.5 M NaOH, 1.5 M NaCl) and renatured for 5 min with the renaturation solution (1.5 M NaCl, 0.5 M TRISHCl, pH 7.4). The filter was washed in 2×SSC (1×SSC: 8.75 g NaCl, 4.4 g Na citrate per 1 l $H_2O$, pH 7.0), dried and baked 30 min at 120° C. in a vacuum oven in order to fix the DNA. The filter was then pre-hybridized with hybridization solution (5×SSC, 1% blocking reagent from Boehringer Mannheim, 0.1% Na-lauryl-sarcosinate, 0.02% sodium dodecylsulfonate) at 32° C. After two hours radioactively marked oligonucleotide was added. The oligonucleotide was obtained from the company MWG Biotech GmbH and the nucleotide sequence was derived from the N-terminal amino acid sequence of the L-hydantoinase from *Arthrobacter aurescens* (Siemann, dissertation 1992).

Oligonucleotide: 5'-ATGTT(C/T)GA(T/C)GT(A/C/T/G) AT(A/C/T)GT-3'

10 pmol of this oligonucleotide were marked with 80 μCi γ-$^{32}$p-ATP and 6 units of polynucleotide kinase in a volume of 10 μl 30 min at 37° C. and the marked oligonucleotide added to the hybridization solution. The mixture was hybridized at 32° C. for 20 hours. The filter was at first washed briefly with 0.2×SSC, 0.1% SDS at room temperature, 30 min at 32° C. and once again with 0.1×SSC, 0.1% SDS 15 min at 32° C. After drying, positive phages were determined via autoradiography. Two were isolated thereby from 2500 phages, which two hybridized with the probe. One of the phages was investigated further.

Transformation of the Recombinant Phage into a Plasmid:

The vector λRESIII contains in addition to the λ genes and the substitution fragment a replication source of the *E. coli* plasmid Rts 1, a kanamycin resistance gene as well as two recognition sequences (res) for a site-specific recombination system (the resolvase from the transposon Tn1721). The phage is inhibited in its multiplication by infection of a specific *E. coli* strain (*E. coli* HB101 F'Lac(::Tn1739 tnpR)), which contains a derivative of this transposon and at the same time the plasmid is cut out together with the substitution fragment via the transposon-coded resolvase from the phage DNA and transformed into a plasmid. Recombinant phages were isolated out of the plaque, which hybridized with the probe as the plaque area was punched out of the agar plate. The material was re-suspended in 0.5 ml SM buffer and 0.1 ml of this phage suspension was mixed with 0.1 ml of an overnight culture of the strain *E. coli* HB101 F'Lac (::Tn1739 tnpR), incubated 5 min at room temperature, added into 2 ml LB medium with 0.1 M isopropyl-β-thiogalactopyranoside and incubated for 45 min on a roller at 37° C. Subsequently, aliquots were plated onto LB agar plates with 50 μg/ml kanamycin and the agar plates incubated overnight at 37° C. Plasmid DNA was isolated from the obtained colonies according to a method described by Kieser (1984) and the plasmid pAW16 obtained thereby. pAW16 contains a 7.6 kb-sized fragment from *Arthrobacter aurescens*. The fragment was completely sequenced with the aid of an ALF sequencer and the AutoRead™ sequencing kits of the Pharmacia company and analyzed with the programs of the GCG software packet. An open reading frame was able to be identified, on account of the identity of the derived amino acid sequence with the sequenced N-terminal end of hydantoinase, as gene hyuH for hydantoinase. A further open reading frame was identified on the end of hyuH, beginning with a GTG start codon of a base in front of the stop codon TGA of the hyuH gene. The derived amino acid sequence of this open reading frame exhibits homology with an N-L-carbamoylase from Bacillus *stearothermophilus* NS1122A (Mukohara et al., 1993) and from *Pseudomonas sp.* NS671 (Watabe et al., 1992). Furthermore, the N-terminal amino acid sequence coincides with the N-terminal sequence of the N-L-carbamoylase from A.s. (Siemann, dissertation, 1992). The gene was designated with hyuC for N-L-carbamoylase.

Expression of HyuC in *E. coli* JM109 via a Promoter which can be Induced with Rhamnose:

For the expression of the N-L-carbamoylase gene hyuC in *E. coli* the gene was amplified via the polymerase chain reaction (PCR). The two primers S956 and S957 were obtained from MWG Biotech GmbH.

S956:
  5'-AGAACATATGTTTGACGTAATAGTTAAGAA-3'
S957: 5'-AAAAGGATCCTCACTTCGACGCCTCGTA-3'

A restriction cleavage site for the enzyme NdeI was added on the N-terminus and a BamHI cleavage site on the C-terminus by the primers. Both cleavage sites are necessary in order to insert the gene behind the rhamnose promoter of the vector pJOE2702 (Volff et al., 1996). Furthermore, the GTG start codon used in *Arthrobacter aurescens* for the translation of the gene was transformed into an ATG start codon.

The reaction was carried out in 100 μl. 1 ng pAW16 DNA, 30 pmol each of the two primers, 0.2 mM dNTP, 16 mM $(NH_4)_2SO_4$, 67 mM TRIS-HCl, pH 8.8, 0.01% Tween, 1.5 mM $MgCl_2$, 0.5 units Taq polymerase were used. The amplification took place in 30 cycles with three stages, 1 min 94° C., 1 min 50° C. and 1.5 min 72° C. in a MiniCycler PTC150, Biozym Diagnostik GmbH. The amplified fragment was purified over a QUIAquick Spin column (Quiagen GmbH). 500 ng of the fragment were treated for 1 h in a volume of 20 μl with 10 units each of the restriction enzyme NdeI and BamHI in the buffer supplied at the same time by the manufacturer. DNA of the vector pJOE2702 was likewise treated with these enzymes under the same conditions. The DNA's were separated on a 0.7% agarose gel and the fragments isolated out of the gel as described above. 20 ng PCR fragment and 20 ng vector were ligated under the conditions described above. *E. coli* JM109 was transformed with the ligated DNA according to a protocol of Chung et al. (1989). The cells were plated onto LB agar plates containing 100 μg/ml ampicillin ($LB_{amp}$). On the following day plasmids were isolated out of ampicillin-resistant colonies and characterized with the restriction enzymes NdeI and BamHI. The plasmid pAW178-2 contained the hyuC gene in the desired orientation under the rhamnose promoter.

Expression of hyuC in *E. coli* JM109/pAW178-2:

1 ml of an overnight culture of *E. coli* JM109/pAW178-2 (FIG. 1) in $LB_{amp}$ is added into 100 ml fresh $LB_{amp}$ medium in a one-liter Erlenmeyer flask and the latter incubated at 30° C. in a water bath under agitation (200 rpm). 1 ml of a 20% rhamnose solution is added to the culture at an optical density of the culture of 0.5 (measured at a wavelength of 600 nm in a photometer) (end concentration 0.2 g/l) and the culture incubated further. After a further 9 h incubation approximately the maximum of the N-L-carbamoylase activity is achieved, a specific activity of 1.8 units/mg raw extract, measured with N-carbamoyl-L-tryptophane as substrate. No activity was found in cultures which had not been induced with rhamnose.

Determination of the Substrate Spectrum of the Rec-L-N-carbamoylase from A.a.

The substrate specificity of the carbamoylase was investigated with homogeneously purified enzyme. The latter was obtained after cell maceration and ion exchange chromatography on Streamline-DEAE- and MonoQ media. A solution of the particular substrate was produced in a concentration of 1.8 mM (exception N-carbamoyl-L-methionine: 50 mM) in 0.1 M TRIS-HCl, pH 8.5 and used instead of the standard substrate in the standard activity test. Instead of the trichloroacetic acid (TCA) used in the standard test for stopping, in the case of the substrates N-formyl-D,L-tryptophane, N-carbamoyl-L-thienylalanine and N-acetyl-D,L-tryptophane heat denaturation was used to terminate the reaction (incubation for 10 min in a boiling water bath) and in the case of the substrate N-carbamoyl-D,L-phenylalanine, addition of 900 μl methanol to 100 μl assay solution was used. The concentration of the amino acid was subsequently determined either by HPLC or calorimetrically after reaction with ninhydrin.

TABLE 1

Determination of the substrate spectrum and of the stereospecificity of the rec-L-N-carbamoylase from A.a.

| Substrate | Product | Activity % | $K_m$ (mM) | Analytic methods |
|---|---|---|---|---|
| N-carbamoyl-L-tryptophane | L-tryptophane | 100 | 0.12 | HPLC colorimetric |
| N-carbamoyl-D-tryptophane | D-Tryptophane | n.n. | | HPLC |
| N-formyl-D-L-tryptophane | L-Tryptophane | 97 | 8.5 | HPLC |
| N-acetyl-D,L-tryptophane | L-Tryptophane | n.n. | | HPLC |
| N-carbamoyl-L-thienylalanine | L-Thienylalanine | 314 | 2.3 | HPLC colorimetric |
| N-carbamoyl-D,L-phenylalanine | L-Phenylalanine | 97 | 0.7 | HPLC |
| N-carbamoyl-D-phenylalanine | D-Phenylalanine | n.n. | | HPLC |
| N-carbamoyl-L-tyrosine | L-Tyrosine | 126 | 0.3 | HPLC |
| N-carbamoyl-L-methionine | L-Methionine | 17 | | HPLC colorimetric |
| N-carbamoyl-L-phenylglycine | L-Phenylglycine | n.n. | | HPLC colorimetric |
| N-carbamoyl-D-phenylglycine | D-Phenylglycine | n.n. | | colorimetric |
| N-carbamoyl-β-alanine | β-Alanine | n.n. | | colorimetric |
| N-carbamoyl-D,L-aspartate | L-Aspartate | n.n. | | colorimetric |
| N-formyl-L-aspartate | L-Aspartate | n.n. | | colorimetric |
| N-carbamoyl-L-glutamate | L-Glutamate | n.n. | | colorimetric |
| N-carbamoyl-L-arginine | L-Arginine | n.n. | | colorimetric | n.n.: can not be detected

Temperature Stability of the rec-L-N-carbamoylase from A.a.

Figure 2:
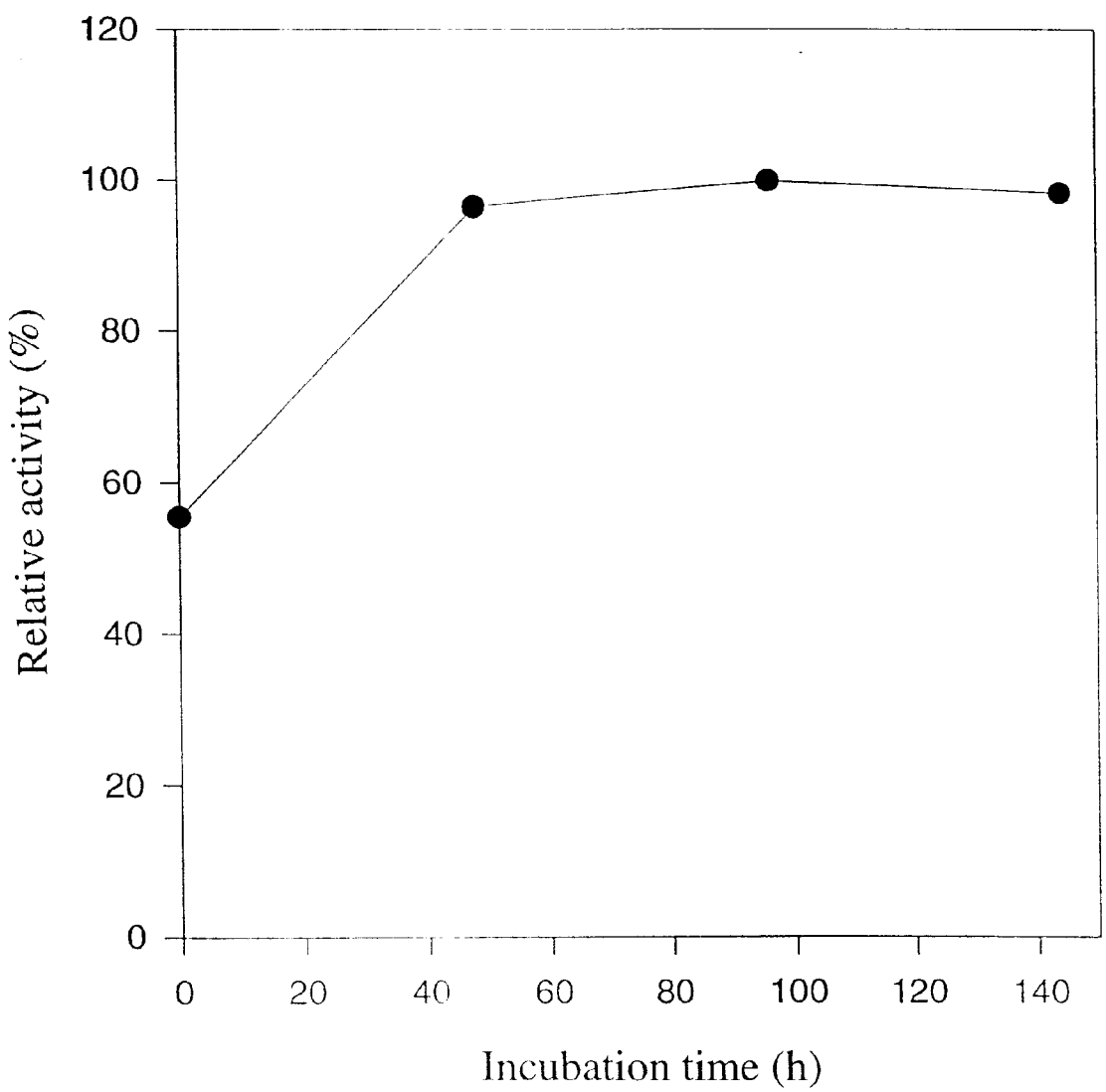
FIG. 2.

The homogeneously purified recombinant L-carbamoylase was stored at 37° C. The standard test for determination of activity was carried out at time intervals of 1–100 h. The initially measured activity remained almost unchanged for over 100 h (FIG. 2).

Immobilization of Rec-L-N-carbamoylase:

250 μl enzyme solution (after the purification, protein concentration: 2.3 mg/ml) is diluted with 19.75 ml of a solution of 1 mM $MnCl_2$ in water (protein end concentration: 0.028 mg/ml). From this solution 4 ml is added to 1.5 g of previously washed EAH sepharose 4B (from Pharamacia Biotech, washing one after the other with 0.1 M phosphate buffer, pH 6.5 and subsequently with a solution of 1 mM $MnCl_2$ in water). After an adsorption phase of 20 min, 545 μl of a coupling solution of 500 mM N-(3-dimethylaminopropyl)-N'-ethyl carbodiimide hydrochloride (EDC) in water, pH 6.0 is added to the batch (end concentration EDC: 60 mM) and agitated in a vertical agitator up to 30 h (preferably 15 h). The matter is filtered by suction and washed three times with 0.2 M TRIS buffer, 0.5 M NaCl, pH 7.0. The immobilized matter is held for one hour in the last wash solution. The matter is washed again (0.1 M TRIS buffer, pH 7.0) and stored in 0.1 M TRIS buffer, 0.1 mM $MnCl_2$, pH 7.0). The activity of the immobilized enzyme was 100% compared to that of the one used.

Enzyme Measurements of N-L-carbamoylase 5 ml of a cell culture induced with rhamnose are centrifuged at 3000 rpm for 5 min in a Heraeus Megafuge, washed with 5 ml buffer (200 mM TRIS-HCl, pH 7.0), re-centrifuged, taken up in 1 ml buffer (200 mM TRIS-HCl, 0.1 mM $MnCl_2$ pH 7.0) and macerated by ultrasound (Ultrasonics Sonicator, microtip, 2×30 sec, duty cycle 50 %). Cell fragments are removed by centrifugation in an Eppendorf centrifuge at 13000 rpm, 10 min. The supernatant, designated as raw extract, is used for the enzyme measurement. 100 μl raw extract or cleaned-up enzyme is mixed with 800 μl 2 mM N-carbamoyl amino acid preheated to 37° C. in 100 mM TRIS-HCl, pH 8.5 and incubated 10 min at 37° C. The reaction is stopped by the addition of 400 μl trichloroacetic acid. The precipitated protein is separated by centrifugation in an Eppendorf centrifuge at 13000 rpm for 10 min. The supernatant is subsequently measured in an HPLC or calorimetrically (ninhydrin). The. separation of the reaction mixture takes place in an HPLC with an RP-18 column, the inobile solvent is 0.3% (V/V) phosphoric acid, 80% methanol, flow rate 1.0 ml/min. The detection takes place by measuring the UV absorption at a wavelength of 280 nm.

Publications cited herein are hereby incorporated by reference.

What is claimed is:

1. An isolated polynucleotide sequence encoding an amino acid sequence of recombinant-L-N-carbamoylase from *Arthrobacter aurescens*, the amino acid sequence being defined by SEQ ID NO:2.

2. The isolated polynucleotide sequence of claim 1 wherein the sequence is SEQ ID NO:1.

3. A vector comprising the isolated polynucleotide sequence according to claim 1.

4. A plasmid comprising the isolated polynucleotide sequence according to claim 1.

5. A host cell comprising the isolated polynucleotide sequence according to claim 1.

* * * * *